(12) United States Patent
Kamen et al.

(10) Patent No.: US 8,715,224 B2
(45) Date of Patent: May 6, 2014

(54) INFUSION PUMP APPARATUS, METHOD AND SYSTEM

(75) Inventors: Dean Kamen, Bedford, NH (US); John M. Kerwin, Manchester, NH (US); Gregory R. Lanier, Jr., Manchester, NH (US); Larry B. Gray, Merrimack, NH (US); Brian D. Tracey, Litchfield, NH (US); David D. B. Cannan, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 13/011,299

(22) Filed: Jan. 21, 2011

(65) Prior Publication Data

US 2011/0313351 A1    Dec. 22, 2011

Related U.S. Application Data

(60) Provisional application No. 61/297,387, filed on Jan. 22, 2010.

(51) Int. Cl.
*A61M 5/168* (2006.01)

(52) U.S. Cl.
USPC ............................................ 604/67; 604/152

(58) Field of Classification Search
USPC .................. 604/67, 131, 151–152, 154–156
See application file for complete search history.

(56) References Cited

U.S. PATENT DOCUMENTS

| | | | | |
|---|---|---|---|---|
| 3,701,345 A * | 10/1972 | Heilman et al. | ............. | 600/432 |
| 4,930,494 A | 6/1990 | Takehana et al. | | |
| 6,551,277 B1 * | 4/2003 | Ford | ............................. | 604/131 |
| 7,498,563 B2 * | 3/2009 | Mandro et al. | ........... | 250/231.13 |
| 2004/0232162 A1 * | 11/2004 | Zimmermann et al. | ........ | 222/63 |
| 2005/0069425 A1 | 3/2005 | Gray et al. | | |
| 2007/0066940 A1 * | 3/2007 | Karunaratne et al. | ........ | 604/152 |
| 2007/0093752 A1 * | 4/2007 | Zhao et al. | .................... | 604/131 |
| 2007/0167931 A1 * | 7/2007 | Waller et al. | .................. | 604/533 |
| 2008/0125700 A1 * | 5/2008 | Moberg et al. | .................. | 604/67 |
| 2008/0308580 A1 * | 12/2008 | Gaydos et al. | ............... | 222/333 |
| 2009/0299277 A1 | 12/2009 | Kamen et al. | | |

FOREIGN PATENT DOCUMENTS

| WO | WO 2007/092618 A2 | 8/2007 |
|---|---|---|
| WO | WO 2007/094833 A1 | 8/2007 |
| WO | WO 2009/083600 A1 | 7/2009 |

OTHER PUBLICATIONS

International Search dated Jan. 12, 2011, received in international patent application No. PCT/US2010/042150, 7 pgs.
International Search Report and Written Opinion dated Jun. 28, 2011, received in international patent application No. PCT/US2010/042150, 15 pgs.

(Continued)

*Primary Examiner* — Quynh-Nhu H Vu
(74) *Attorney, Agent, or Firm* — Michelle Saquet Temple

(57) ABSTRACT

An infusion pump system is disclosed. The system includes a syringe having a plunger within the syringe barrel, the syringe having an exit end, at least one temperature determination device adjacent to the syringe, at least one device to determine the distance the plunger has moved with respect to the syringe barrel, and a pump processor in communication with the at least one temperature determination device and the at least one optical sensor, wherein when the controller determines a change in temperature and a corresponding plunger movement, the controller increases or decreases a preprogrammed basal rate of the infusion pump by a predetermined amount for a predetermined time.

22 Claims, 9 Drawing Sheets

(56) References Cited

OTHER PUBLICATIONS

International Search Report and Written Opinion dated Jun. 29, 2011, received in international patent application No. PCT/US2011/022073, 13 pgs.
International Search Report and Written Opinion dated Oct. 12, 2011, received in international patent application No. PCT/US2011/022051, 20 pgs.
International Preliminary Report on Patentablility & Written Opinion, dated Jan. 26, 2012, received in International patent application No. PCT/US2010/042150, 10 pgs.
International Preliminary Report on Patentablility & Written Opinion, dated Aug. 2, 2012, received in International patent application No. PCT/US2011/022051, 14 pgs.
International Preliminary Report on Patentablility & Written Opinion, dated Aug. 2, 2012, received in International patent application No. PCT/US2011/022073, 9 pgs.

* cited by examiner

INFUSION PUMP APPARATUS, METHOD AND SYSTEM

CROSS REFERENCE TO RELATED APPLICATION(S)

The present application is a Non-Provisional Application which claims priority from U.S. Provisional Patent Application Ser. No. 61/297,387, filed Jan. 22, 2010 and entitled Infusion Pump Apparatus, Method and System, which is hereby incorporated herein by reference in its entirety.

TECHNICAL FIELD

The present disclosure relates to medical devices and more particularly, to an infusion pump apparatus, methods and systems.

BACKGROUND INFORMATION

Many potentially valuable medicines or compounds, including biologicals, are not orally active due to poor absorption, hepatic metabolism or other pharmacokinetic factors. Additionally, some therapeutic compounds, although they can be orally absorbed, are sometimes required to be administered so often it is difficult for a patient to maintain the desired schedule. In these cases, parenteral delivery is often employed or could be employed.

Effective parenteral routes of drug delivery, as well as other fluids and compounds, such as subcutaneous injection, intramuscular injection, and intravenous (IV) administration include puncture of the skin with a needle or stylet. Insulin is an example of a therapeutic fluid that is self-injected by millions of diabetic patients. Users of parenterally delivered drugs may benefit from a wearable device that would automatically deliver needed drugs/compounds over a period of time.

To this end, there have been efforts to design portable and wearable devices for the controlled release of therapeutics. Such devices are known to have a reservoir such as a cartridge, syringe, or bag, and to be electronically controlled. These devices suffer from a number of drawbacks including the malfunction rate. Reducing the size, weight and cost of these devices is also an ongoing challenge. Additionally, these devices often apply to the skin and pose the challenge of frequent re-location for application.

SUMMARY

In accordance with one aspect of the present invention, an infusion pump system is disclosed. The system includes a syringe having a plunger within the syringe barrel, the syringe having an exit end, at least one temperature determination device adjacent to the syringe, at least one device to determine the distance the plunger has moved with respect to the syringe barrel, and a pump processor in communication with the at least one temperature determination device and the at least one optical sensor, wherein when the controller determines a change in temperature and a corresponding plunger movement, the controller increases or decreases a preprogrammed basal rate of the infusion pump by a predetermined amount for a predetermined time.

Some embodiments may include one or more of the following. Wherein when the pump processor determines an upward change in temperature and a corresponding plunger movement away from the syringe exit, the pump processor increases the preprogrammed basal rate of the infusion pump by a predetermined amount for a predetermined time. Wherein when the pump processor determines an downward change in temperature and a corresponding plunger movement towards the syringe exit, the pump processor decreases the preprogrammed basal rate of the infusion pump by a predetermined amount for a predetermined time. Wherein the at least one temperature determination device is a thermistor. Wherein the at least one device to determine the distance the plunger has moved with respect to the syringe barrel is an optical sensor.

In accordance with one aspect of the present invention, an infusion pump system is disclosed. The infusion pump system includes a syringe having an exit end and a plunger movable within the syringe, at least one temperature determination device, at least one device to determine the effect of a temperature change on the movement of the plunger, and a pump processor to compensate for the movement of the plunger based on a temperature change.

Some embodiments may include one or more of the following. Wherein the pump processor commands the plunger to move away from the syringe exit by a predetermined distance to compensate for the movement of the plunger based on a temperature change. Wherein the pump processor decreases a preprogrammed basal rate for a predetermined amount of time by a predetermined amount based on the movement of the plunger based on a temperature change. Wherein the at least one temperature determination device is located adjacent to the syringe. Wherein the at least one temperature determination device is a thermistor. Wherein the at least one device to determine the effect of the temperature change on the movement of the plunger is an optical sensor.

In accordance with one aspect of the present invention, an infusion pump system is disclosed. The infusion pump system includes a syringe having an exit end and a plunger movable within the syringe, at least one temperature determination device, at least one device to detect the effect of a temperature change on the movement of the plunger, and a pump processor in communication with the at least one temperature determination device and the at least one device to detect the effect of a temperature change on the movement of the plunger.

Some embodiments may include one or more of the following. Wherein the at least one device to detect the effect of a temperature change on the movement of the plunger is a flow sensor located downstream from the syringe exit. Wherein the at least one device to detect the effect of a temperature change on the movement of the plunger is an occlusion device located downstream from the syringe exit wherein the occlusion device occludes a flow path, the occlusion device controlled by the pump processor. Wherein the at least one device to detect the effect of a temperature change on the movement of the plunger is at least one binary valve located downstream from the syringe exit wherein the at least one binary valve occludes a flow path, the at least one binary valve controlled by the pump processor. Wherein the at least one device to detect the effect of a temperature change on the movement of the plunger is a strain beam located in force relationship with the plunger. Wherein the at least one device to detect the effect of a temperature change on the movement of the plunger is at least one potentiometer. Wherein the plunger further comprising a predetermined volume of a material which undergoes a phase change during a temperature change event. Wherein the material is wax and the wax and wherein the wax undergoes a phase change, moves the plunger forward a predetermined distance whereby the resulting change compensates for the change in volume of the syringe due to a temperature change.

In accordance with one aspect of the present invention, an infusion pump system is disclosed. The infusion pump system includes a syringe having an exit end and a plunger movable within the syringe, an occluder located downstream from the syringe exit, at least one temperature determination device, and a pump processor in communication with the occluder and the at least one temperature determination device, wherein the pump processor activates the occluder based on the temperature signals from the at least one temperature determination device.

Some embodiments may include one or more of the following. Wherein when the at least one temperature determination device signal indicates a temperature change that exceeds a predetermined threshold, the pump controller activates the occluder. Wherein the pump controller activates the occluder between pump deliveries.

In accordance with one aspect of the present invention, a method for the delivery of fluid by an infusion pump is disclosed. The method includes determining the distance a plunger should move to deliver a target volume, determining the volume of fluid delivered as the temperature changes, determining the target plunger position, and adjusting the target plunger position based on the actual movement of a temperature change.

In accordance with one aspect of the present invention, a method for the delivery of fluid by an infusion pump is disclosed. The method includes determining a temperature change, determining a rate of change exceeds a threshold, and adjusting a basal rate.

In accordance with one aspect of the present invention, a system, method and apparatus for temperature compensation in an infusion pump and an infusion pump with temperature compensation is disclosed. The system includes at least one temperature sensor, the temperature sensor communicating with at least one processor. The processor determines the target plunger position and, based at least at least upon the communication from the temperature sensor, may modify the target plunger position based on the temperature sensed.

Some embodiments may include one or more of the following: an occluder and/or a binary exit valve; at least one optical sensor; at least one flow sensor.

In accordance with one aspect of the present invention, a system for temperature compensation in an infusion pump is disclosed. The system includes a characterization of the infusion pump at various temperatures including characterization of the volume of fluid pumped, either request or based on a temperature change. Also, at least one temperature sensor, the temperature sensor to collect data which indicates the temperature either inside or outside the infusion pump, the temperature sensor communicating the data to a processor. The processor compares the data to the characterization and may determine to adjust the target plunge position based on the temperature. Some embodiments may include an occluder and/or a binary exit valve.

In accordance with one aspect of the present invention, an apparatus for insulating an infusion pump is disclosed. The apparatus includes a housing of a predetermined size to accommodate an infusion pump, the housing having at least one insulating layer. The housing including an opening of a predetermined size to accommodate tubing.

Some embodiments may include one or more of the following: a strap; wherein the strap is adjustable; wherein the strap includes a buckle; wherein the apparatus includes an insulating layer that is made from a material which, when wetted and refrigerated or frozen, provides a cooling effect onto the housing.

In accordance with one aspect of the present invention, an infusion pump with a heater including a heating device and at least one temperature sensor such that the temperature is communicated to a processor which controls the heating device and activates the heating device for a sufficient time to maintain the temperature of the infusion pump at a predetermined temperature.

In accordance with one aspect of the present invention, a temperature label for a vial of fluid is disclosed. The temperature label visually indicates the temperature of the vial. Some embodiments of this aspect of the invention may include wherein the temperature label is non-reversible.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein.

DETAILED DESCRIPTION OF THE EXEMPLARY EMBODIMENTS

Definitions

Figure 1A:
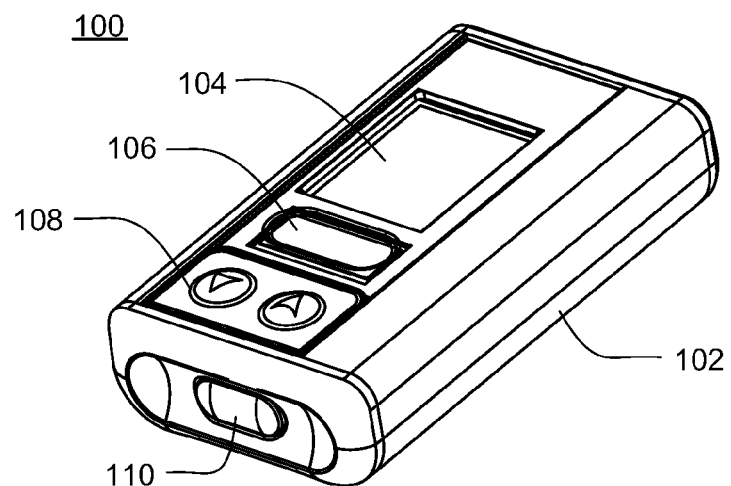
FIGS. 1A-1B are front and back isometric view of an embodiment of an infusion pump.
Figure 1B:
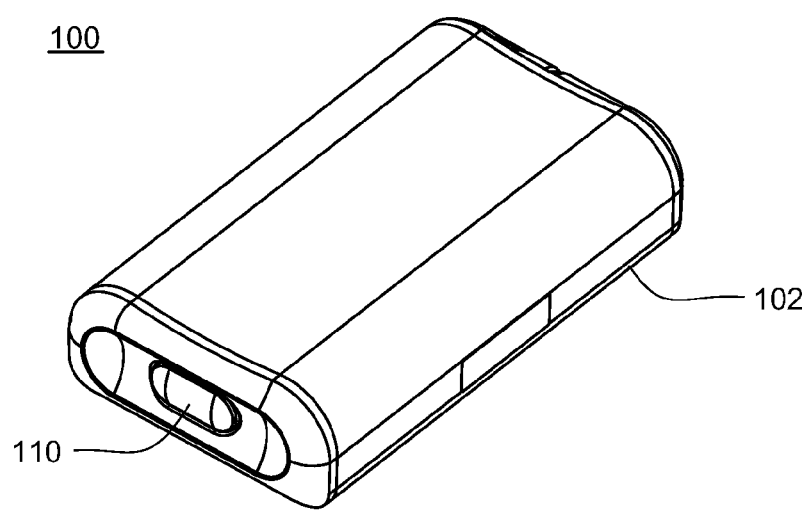
Figures 1C, 1D, 1E, 1F:
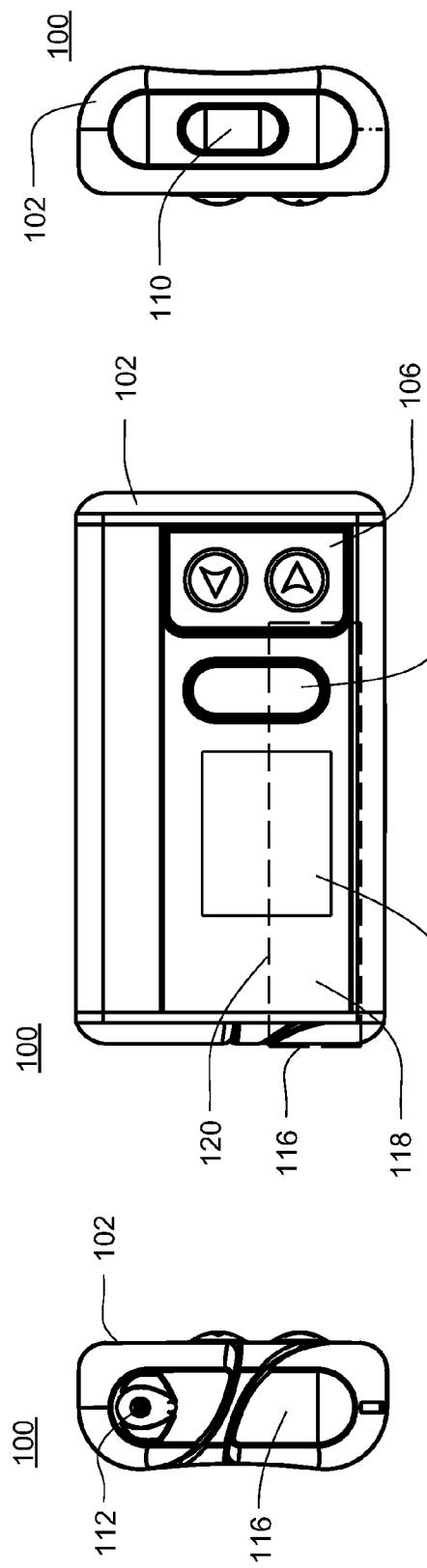
FIGS. 1C-1E are side and front views of the infusion pump assembly of FIG. 1.
FIG. 1F is a front isometric view of the infusion pump assembly of FIG. 1.

As used in this description and the accompanying claims, the following terms shall have the meanings indicated, unless the context otherwise requires:

A "device" shall mean a medical device, which includes, but is not limited to, an infusion pump and/or a controller, i.e., a device for wireless control of another medical device. In some embodiments, the word "device" is used interchangeably with "pump", "infusion pump" and/or "controller" and/or "Companion" and/or "remote controller device" and/or "remote controller assembly".

A "Companion" shall mean a device for wireless control of another medical device. In the exemplary embodiments, the Companion may also include a glucose meter/strip reader.

An "input" of a device includes any mechanism by which a user of the device or other operator/caregiver may control a function of the device. User inputs may include mechanical arrangements (e.g., switches, pushbuttons, jogwheel(s)), electrical arrangements (e.g., a slider, touch screen), wireless interfaces for communication with a remote controller (e.g., RF, infrared), acoustic interfaces (e.g., with speech recognition), computer network interfaces (e.g., USB port), and other types of interfaces.

A "button" in the context of an input such as the so-called "bolus button" discussed below may be any type of user input capable of performing a desired function, and is not limited to a pushbutton, a slider, switch, touch screen or a jog wheel.

An "alarm" includes any mechanism by which an alert may be generated to a user or third party. Alarms may include audible alarms (e.g., a speaker, a buzzer, a speech generator), visual alarms (e.g., an LED, an LCD screen), tactile alarms (e.g., a vibrating element), wireless signals (e.g., a wireless transmission to a remote controller or caretaker), or other mechanism. Alarms may be generated using multiple mechanisms simultaneously, concurrently, or in a sequence, including redundant mechanisms (e.g., two different audio alarms) or complementary mechanisms (e.g., an audio alarm, a tactile alarm, and a wireless alarm).

"Fluid" shall mean a substance, a liquid for example, that is capable of flowing through a flow line.

A "user" includes a person or animal who receives fluid from a fluid delivery device, whether as part of a medical treatment or otherwise, or a caregiver or third party involved in programming the device or otherwise interacting with the device to infuse fluid to another.

"Cannula" shall mean a disposable device capable of infusing fluid to a user. A cannula as used herein may refer to a traditional cannula or to a needle.

"Disposable" refers to a part, device, portion or other that is intended to be used for a fixed duration of time, then discarded and replaced.

"Reusable" refers to a portion that is intended to have an open-ended duration of use.

"Acoustic volume measurement" shall mean quantitative measurement of a relevant volume using acoustical techniques such as those described in U.S. Pat. Nos. 5,349,852 and 5,641,892, which are hereby incorporated by reference herein in their entireties, as well as other techniques.

A "temperature sensor" includes any temperature determination device/mechanism for measuring temperature and communicating temperature information to a controller and/or to a pump processor. The devices described herein may include one or more temperature sensors for measuring such things as including, but not limited to, one or more of the following: user skin temperature, AVS temperature, ambient temperature, internal pump temperature, plunger temperature, drive train temperature and fluid temperatures.

An exemplary use of embodiments of the devices, methods and systems described here is for the delivery of insulin to people living with diabetes, but other uses include delivery of any fluid, as described above. Fluids include analgesics to those in pain, chemotherapy to cancer patients and enzymes to patients with metabolic disorders. Various therapeutic fluids may include small molecules, natural products, peptide, proteins, nucleic acids, carbohydrates, nanoparticulate suspensions, and associated pharmaceutically acceptable carrier molecules. Therapeutically active molecules may be modified to improve stability in the device (e.g., by pegylation of peptides or proteins). Although illustrative embodiments herein describe drug-delivery applications, embodiments may be used for other applications including liquid dispensing of reagents for high throughput analytical measurements such as lab-on-chip applications and capillary chromatography. For purposes of description below, terms "therapeutic", "insulin" or "fluid" are used interchangeably, however, in other embodiments, any fluid, as described above, may be used. Thus, the device and description included herein are not limited to use with therapeutics.

Some embodiments of the fluid delivery device are adapted for use by people living with diabetes and/or their caregivers. Thus, in these embodiments, the devices, methods and systems work to delivers insulin which supplements or replaces the action of the person living with diabetes' (referred to as the user) pancreatic islet beta cells. Embodiments adapted for insulin delivery seek to mimic the action of the pancreas by providing both a basal level of fluid delivery as well as bolus levels of delivery. Basal levels, bolus levels and timing may be set by the user or a caregiver by using a wireless handheld user interface or directly by using a pump. Additionally, basal and/or bolus levels may be triggered or adjusted in response to the output of a glucose meter, which in the exemplary embodiments, is integral to the controller. In other embodiments, the controller additionally includes a glucose monitoring device which receives data from a blood glucose sensor. In some embodiments, a bolus may be triggered by a user using a designated button or other input means located on a device, i.e., on the controller and/or on an infusion pump. In still other embodiments, the bolus or basal may be programmed or administered through a user interface located either on the fluid delivery device/infusion pump and/or on the controller.

With respect to the names given to screens and types of screens, as well as proper names given to various features, throughout various embodiments, these terms may vary.

The systems and methods described herein may be used to control an infusion pump. For purposes of this description, the various embodiments of the user interface and the infusion pump may be described with reference to an insulin pump, or a pump which infuses insulin. However, it should be understood that the user interface may be on an infusion pump and/or on a controller. Additionally, where the description pertains to an infusion pump "screen", this "screen" may also appear on a controller, or may appear on a controller in lieu of a pump.

Infusion pumps contemplated by this description include a pump which may pump any fluid, including, but not limited to, a therapeutic fluid, which includes, but is not limited to, insulin. Thus, where this description describes the exemplary embodiment as pertaining to insulin, this is meant merely for descriptive purpose only as the device is not intended to be limited to insulin. Other fluids are also contemplated. In some embodiments, the methods, systems and devices described herein may be used in conjunction with insulin "pens" and/or fluid delivery "pens", which are known in the art.

The infusion pump may be any infusion pump, for example, but not limited to, the pump devices shown and described with respect to FIGS. 1A-1F and those incorporated herein by reference, and include, but are not limited to, those incorporated herein by reference. In the various exemplary embodiments, the infusion pump is a syringe-pump, i.e., the fluid is pumped or delivered to the user when a plunger advances in a syringe, pushing the fluid inside the syringe into a cannula. Where the cannula is connected to a user (i.e., the cannula is within the user's subcutaneous region) the fluid is delivered subcutaneously to the user.

In the exemplary embodiment, the infusion pump includes hardware for wireless RF communication with a controller. However, in various embodiments, the infusion pump may be any infusion pump. Referring to FIGS. 1A-1F and 2A-2D, in some exemplary embodiments, the infusion pump may include a display assembly 104, however, in other exemplary embodiments, such as those shown in FIGS. 2A-2D, the infusion pump may not include a display assembly. In these embodiments, a display assembly which may be similar to the one shown in FIGS. 1A, 1D and 1F, or may be larger or smaller, is included on a controller or companion device. An embodiment of the controller or companion device is shown in FIG. 3.

Referring to FIGS. 1A-1F, an embodiment of an infusion pump assembly 100 that may be housed within enclosure assembly 102 is shown. Infusion pump assembly 100 may include a display system 104 that may be visible through the enclosure assembly 102. One or more switch assemblies/input devices 106, 108, 110 may be positioned about various portions of the enclosure assembly 102. The enclosure assembly 102 may include infusion port assembly 112 to which cannula assembly 114 may be releasably coupled. A removable cover assembly 116 may allow access to a power supply cavity 118 (shown in phantom on FIG. 1D).

Referring to the infusion pump assemblies shown in FIG. 1A-1F, infusion pump assembly 100 may include processing logic (not shown), which may be referred to as the pump processor, that executes one or more processes that may be required for infusion pump assembly 100 to operate properly. Processing logic may include one or more microprocessors (not shown), one or more input/output controllers (not shown), and cache memory devices (not shown). One or more data buses and/or memory buses may be used to interconnect processing logic with one or more subsystems. In some embodiments, at least one of the subsystems shown in FIG. 3 is also included in the embodiment of the infusion pump assembly 200 shown in FIGS. 2A-2D.

Referring now to FIGS. 1A-1F and FIG. 3, examples of the subsystems interconnected with processing logic 400 may include but are not limited to memory system 402, input system 404, display system 406, vibration system 408, audio system 410 motor assembly 416, force sensor 412, temperature sensor (not shown) and displacement detection device 418 (which may be referred to as a device to determine and/or detect the distance the plunger has moved with respect to the syringe barrel/syringe). Infusion pump assembly 100 may include primary power supply 420 (e.g. a battery) configured to be removable installable within power supply cavity 118 and to provide electrical power to at least a portion of processing logic 400 and one or more of the subsystems (e.g., memory system 402, input system 404, display system 406, vibration system 408, audio system 410, motor assembly 416, force sensor 412, and displacement detection device 418).

Infusion pump assembly 100 may include reservoir assembly 430 configured to contain infusible fluid 422. In some embodiments, reservoir assembly 430 may be a reservoir assembly similar to that described in U.S. Pat. No. 7,498,563, issued Mar. 3, 2009 and entitled Optical Displacement Sensor for Infusion Devices, which is herein incorporated by reference in its entirety, and/or as described in U.S. Pat. No. 7,306,578, issued Dec. 11, 2007 and entitled Loading Mechanism for Infusion Pump; PCT Application Serial No. PCT/US2009/060158, filed Oct. 9, 2009 and entitled Infusion Pump Assembly; and U.S. patent application Ser. No. 12/249,882, filed Oct. 10, 2008 and entitled Infusion Pump Assembly, now U.S. Publication No. US-2010-0094222, published Apr. 15, 2010 and entitled Infusion Pump Assembly, all of which are hereby incorporated herein in their entireties. In other embodiments, the reservoir assembly may be any assembly in which fluid may be acted upon such that at least a portion of the fluid may flow out of the reservoir assembly, for example, the reservoir assembly, in various embodiments, may include but is not limited to: a barrel with a plunger, a cassette or a container at least partially constructed of a flexible membrane.

Plunger assembly 424 may be configured to displace infusible fluid 422 from reservoir assembly 430 through cannula assembly 450 (which may be coupled to infusion pump assembly 100 via infusion port assembly 424) so that infusible fluid 422 may be delivered to user 454. In this particular embodiment, plunger assembly 424 is shown to be displaceable by partial nut assembly 426, which may engage lead screw assembly 428 that may be rotatable by motor assembly 416 in response to signals received from processing logic 400. In this particular embodiment, the combination of motor assembly 416, plunger assembly 424, partial nut assembly 426, and lead screw assembly 428 may form a pump assembly that effectuates the dispensing of infusible fluid 422 contained within reservoir assembly 430. An example of partial nut assembly 426 may include but is not limited to a nut assembly that is configured to wrap around lead screw assembly 426 by e.g., 30 degrees. In some embodiments, the pump assembly may be similar to one described in U.S. Pat. No. 7,306,578, issued Dec. 11, 2007 and entitled Loading Mechanism for Infusion Pump; U.S. patent application Ser. No. 12/249,882, filed Oct. 10, 2008 and entitled Infusion Pump Assembly, now U.S. Publication No. US-2010-0094222, published Apr. 15, 2010 and entitled Infusion Pump Assembly; and U.S. patent application Ser. No. 12/249,891, filed Oct. 10, 2008 and entitled Infusion Pump Assembly, now U.S. Publication No. US-2009-0099523 published Apr. 16, 2009 and entitled Infusion Pump Assembly, all of which are herein incorporated by reference in their entireties.

User Interface

Throughout this description, screens may be referenced with respect to the "pump" or "Companion" or "Controller". However, in various embodiments, a similar screen or a similar method may be accomplished on another device. For example, where the screen or method is referenced with respect to the "pump", a similarly functional screen or method may be used on the "Companion" or "Controller" in other embodiments. As this description includes embodiments related to both pumps having displays and pumps having no displays, it should be evident that where the embodiment includes an infusion pump without a display, any screens will be visible on a Companion or Controller. Similarly, where a method requires an interaction between the user and the pump, the interaction may be accomplished via a switch assembly on the pump where the pump is an infusion pump without a display.

Processing logic which in some embodiments, includes at least one element as shown in described with respect to FIG. 3, is used to receive inputs from a user or caregiver. The user or caregiver uses one or more input devices or assemblies, including but not limited to, one or more of the following: button/switch assembly, slider assemblies, including, but not limited to, capacitive sliders (which may include, for example, including but not limited to any slider described in U.S. patent application Ser. No. 11/999,268, filed Dec. 4, 2007 and entitled Medical Device Including a Slider Assembly, now U.S. Publication No. US-2008-0177900, published Jul. 24, 2008; and entitled Medical Device Including a Slider Assembly, all of which are hereby incorporated herein by reference in their entireties, jog wheel and/or touch screen. The infusion device additionally received inputs from internal systems, including but not limited to occlusion detection process 438, confirmation process 440, volume measurement technology (e.g., acoustic volume sensing). Using these inputs, the infusion device produces outputs, for example including, but not limited to, infusion fluid delivery to the user or comments, alerts, alarms or warnings to the user. The inputs are thus either directly from the user to the pump, directly from the pump systems to the processing logic, or from another device, e.g., a remote controller device (described in more detail below), to the pump. The user or caregiver interaction experience thus includes, but is not limited to, one or more of the following: interaction with a display (either on the infusion pump device itself or a remote controller device or both), which includes but is not limited to, reading/seeing text and/or graphics on a display, direct interaction with a display, for example, through a touch screen, interaction with one or more buttons, sliders, jog wheels, one or more glucose strip readers, and sensing either through touch sensation or audio, one or more vibration motors, and/or an audio system. Thus, the term "user interface" is used to encompass all of the systems and methods a user or caregiver interacts with the infusion pump, to control the infusion pump.

Figure 2:
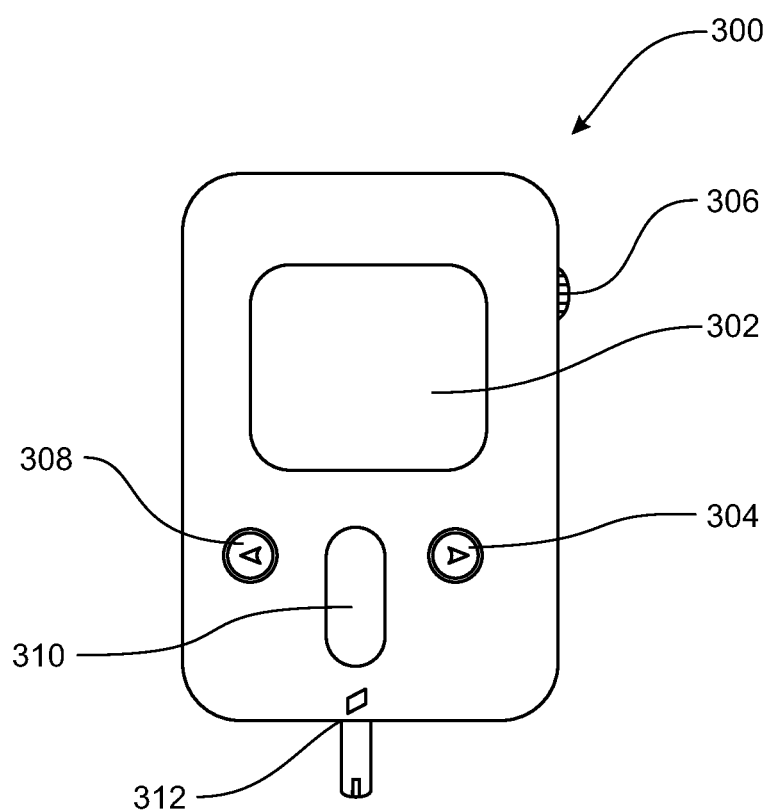
FIG. 2 is an illustrative view of one embodiment of a remote control assembly.
Figure 3:
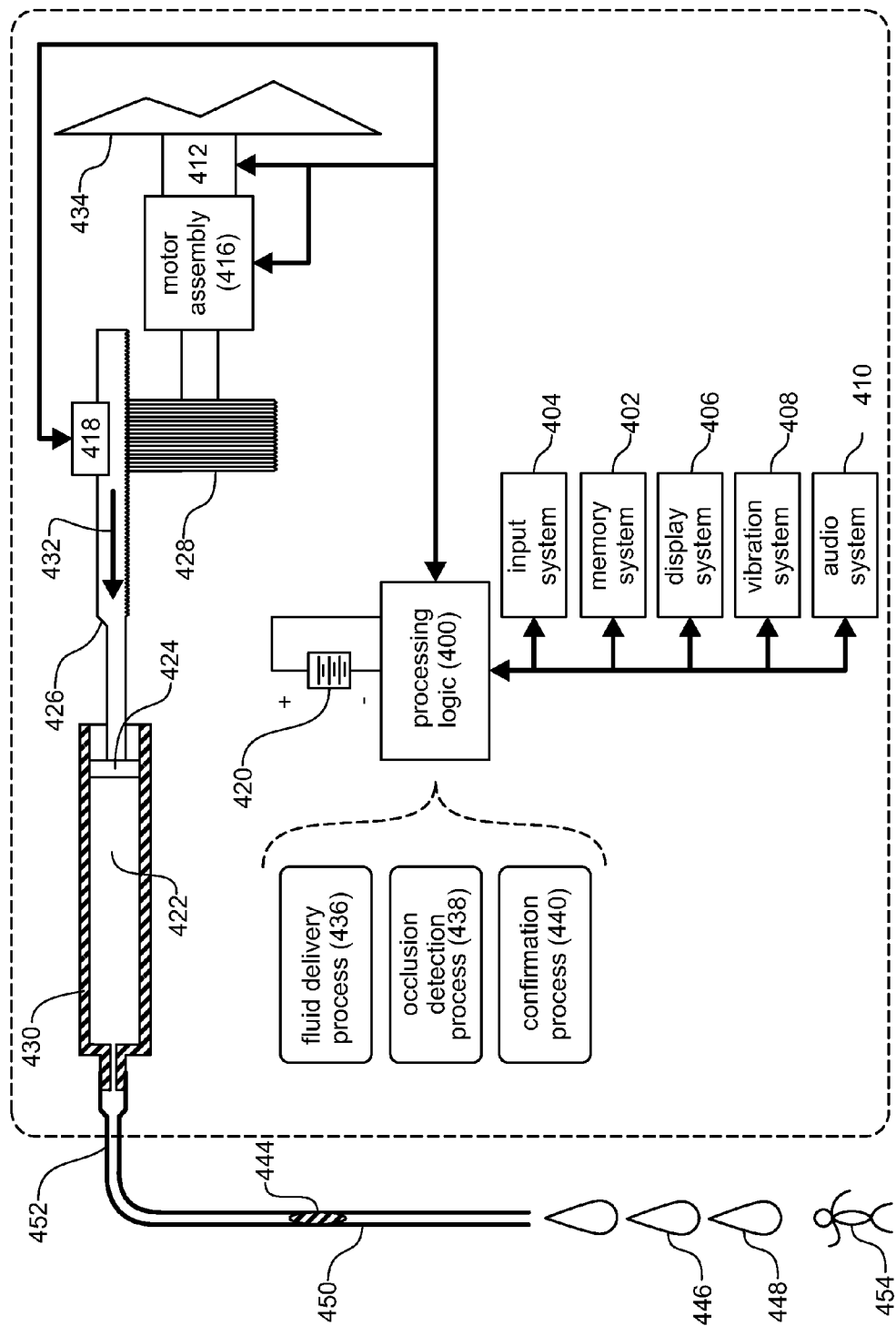
FIG. 3 is a diagrammatic view of the infusion pump assembly of FIG. 1.

Referring now to FIG. 2, in some embodiments of the infusion pump system, the infusion pump may be remotely controlled using a remote controller assembly 300, also referred to as a controller or a companion. Remote control assembly 300 may include all, or a portion of, the functionality of the infusion pump assembly shown in FIGS. 1A-1F, itself. Thus, in some exemplary embodiments of the above-described infusion pump assembly, the infusion pump assembly (not shown, see FIGS. 1A-1F, amongst other FIGS.) may be configured via remote control assembly 300. In these particular embodiments, the infusion pump assembly may include telemetry circuitry (not shown) that allows for communication (e.g., wired or wireless) between the infusion pump assembly and e.g., remote control assembly 300, thus allowing remote control assembly 300 to remotely control infusion pump assembly 100. Remote control assembly 300 (which may also include telemetry circuitry (not shown) and may be capable of communicating with infusion pump assembly) may include display assembly 302 and an input assembly, which may include one or more of the following: an input control device (such as jog wheel 306, slider assembly 310, or another conventional mode for input into a device), and switch assemblies 304, 308. Thus, although remote control assembly 300 as shown in FIG. 2 includes jog wheel 306 and slider assembly 310, some embodiments may include only one of either jog wheel 306 or slider assembly 310, or another conventional mode for input into a device. In embodiments having jog wheel 306, jog wheel 306 may include a wheel, ring, knob, or the like, that may be coupled to a rotary encoder, or other rotary transducer, for providing a control signal based upon, at least in part, movement of the wheel, ring, knob, or the like.

Remote control assembly 300 may include the ability to pre-program basal rates, bolus alarms, delivery limitations, and allow the user to view history and to establish user preferences. Remote control assembly 300 may also include a glucose strip reader 312.

During use, remote control assembly 300 may provide instructions to the infusion pump assembly via a wireless communication channel established between remote control assembly 300 and the infusion pump assembly. Accordingly, the user may use remote control assembly 300 to program/configure the infusion pump assembly. Some or all of the communication between remote control assembly 300 and the infusion pump assembly may be encrypted to provide an enhanced level of security.

Figure 6:
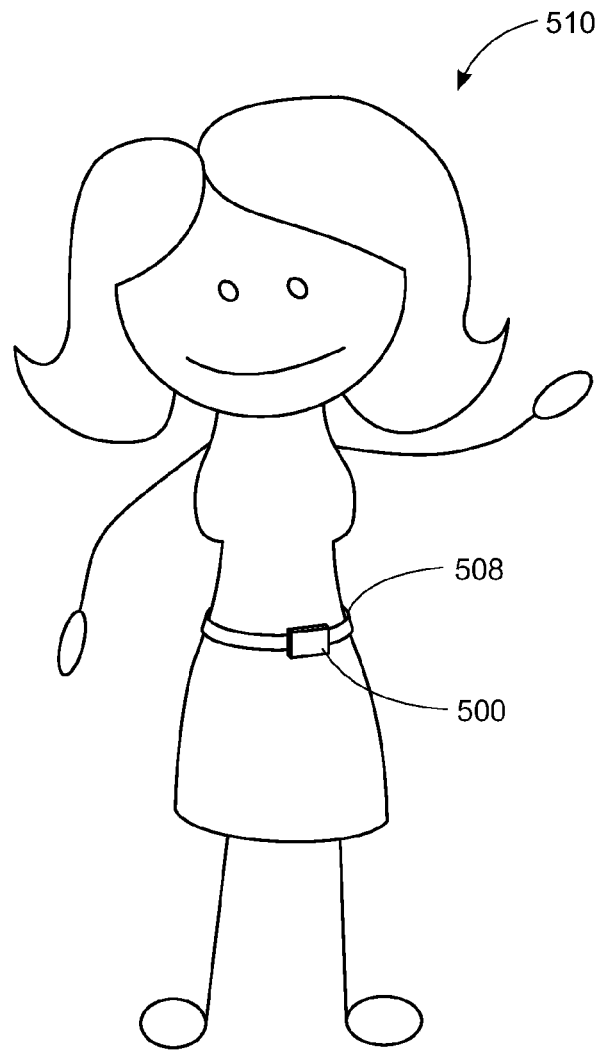
FIG. 6 is an illustration of one embodiment of a user wearing a holder.

In the exemplary embodiments of the user interface, the user interface may require user confirmation and user input. The exemplary embodiments of the user interface are centered on ensuring the user knows the effect of various interactions on the pump. Many examples will be presented throughout this description of the pump communicating the result of the user's actions to the user. These features ensure the user understands their actions and therefore, imparts greater safety onto the user. One such example is throughout the exemplary embodiment of the user interface, where the user presses the back button on a screen after a value has been changed, the user interface displays the Cancel Changes confirmation screen, as shown in FIG. 6. If the user selects "Yes", the user interface discards any pending changes, closes the confirmation screen and goes back to the previous screen (i.e., the screen previous to the screen where the user pressed the Back button). When the action selection is "No", on the "Cancel Changes?" confirmation screen, the user presses the enter button or other depending on the embodiment, and the user interface closes the confirmation screen and returns to the screen with pending changes. This feature prevents the outcome where the user assumes the changes have been implemented, but in fact, they have not been. Thus, this feature prevents that circumstance and ensures the user understands that the changes have not been implemented.

Temperature

In various embodiments of the infusion pump, the user may wear the infusion pump either attached to a belt, attached to another article or clothing or a garment such that the device is worn on the body, or, in some embodiments, attached to an undergarment, in a pocket or, in some embodiments, attached to the skin of the user. The user generally wears the infusion pump as close to twenty-four (24) hours a day as possible, and in some cases, removing the device for short periods of time, for example, but not limited to, during an MRI or other treatment that may effect the device and/or while showering/bathing. Thus, during the normal course of the user's wearing the infusion pump, the infusion pump may be exposed to various temperatures, including, temperature swings, which may include positive temperature swings and/or negative temperature swings. These temperature swings may be the result of the user stepping out of doors, into a cold room, into a hot room and/or under a blanket or other warming agent.

The fluid contained in the reservoir while in the pump, which, as discussed above, may include, but is not limited to insulin, has a thermal expansion coefficient which may be referred to as a general volumetric thermal expansion coefficient. Thus, during a temperature swing/differential/change, whether positive or negative, the fluid, or insulin, will expand or contract. Various factors may contribute to the expansion or contraction of the fluid including but not limited to the rate of change of the temperature. Thus, in some embodiments, the amount of expansion or contraction may be a function of the temperature.

Additionally, in various embodiments of the various embodiments of the devices described, the components of the pumps also have thermal expansion coefficients. These thermal expansion coefficients may vary depending on the material. Thus, where the various components are made from different materials, the thermal expansion coefficients may vary.

In some embodiments, a change in temperature may affect a thermal expansion or thermal contraction of the fluid and/or one or more components of the infusion pump. For example, but not limited to, an increase in temperature may cause an increase in the diameter of the reservoir/syringe 430 (for illustration only, please refer to FIG. 3). This may be because the relative thermal expansion of the syringe compared with the fluid governs whether fluid is delivered or pulled back. Thus, this in turn may cause any fluid/insulin in the cannula 450 to flow backwards, towards the reservoir 430. In this case, a volume of fluid/insulin is pulled back into the reservoir. Thus, a subsequent request for a delivery by processing logic 400 may only result in this retracted volume being delivered to the user. Thus, a volume of fluid/insulin (the retracted volume) has not been delivered to the user without request or knowledge by the user. Another example includes temperature decrease. In some embodiments, a temperature decrease may cause the reservoir 430 to decrease in diameter, causing fluid/insulin to flow to the cannula 450. Thus, an unintended bolus volume is delivered to this user. In this case, fluid/insulin has been delivered to the user without request or knowledge by the user.

Thus, in the first example, the user may receive less fluid/insulin than is required or requested and thus, may experience hyperglycemia. In the second example, the user may receive more fluid/insulin than is required or requested and thus, may experience hypoglycemia. In either example, the user receives a fluid/insulin volume that is not the same as the requested or programmed therapy and is not notified of the disparity.

In these examples, the reservoir is assumed to be a cylinder. Below is a mathematical model of the change in volume of a cylinder (assuming a constant coefficient of linear expansion, α). This is a model for explanation purposes. Additional mathematical models may be determined to accommodate additional assumptions, for example, a shape other than a cylinder, or a syringe with a movable plunger.

$$\Delta V = V(3\alpha\Delta T + 3\alpha^2 \Delta T^2 + \alpha^3 \Delta T^3) \quad [EQ\#1]$$

Which may be simplified assuming $\alpha\Delta T \ll 1$ to:

$$\frac{\Delta V}{V} \approx 3\alpha\Delta Y \quad [EQ\#2]$$

Thus, the volume change of a cylinder made from polypropylene where the temperature changes from 30 C to 10 C for polypropylene, which is a material with linear coefficient of linear expansion $$\frac{\Delta V}{V} \approx 3\left(86 \times 10^{-6} \frac{cm}{cm \cdot K}\right)(20K) = 0.52\% \quad [EQ\#3]$$

would be:

$$\alpha = 86 \times 10^{-6} \frac{cm}{cm \cdot K},$$

The change in specific volume for water between 30 C and 10 C is about 0.40%. The difference between the two (about 0.12%) applied to a 3 cc syringe or reservoir would be about 3.6 μL. However, in addition, the syringe plunger may move in response to the thermal expansion depending on the plunger material and the relationship of the syringe in the pump (e.g., the design of the syringe retention in the pump).

Therefore, there may be a desire to minimize the effect of temperature on the delivery of fluid. Thus, it may be desired to limit or minimize, and/or characterize, the thermal expansion of the fluid and/or one or more of the components of the infusion pump. The systems, methods and apparatus described to minimize the effect of temperature on the thermal expansion of the fluid and/or one of more of the components of the infusion pump may include one or more of the following exemplary embodiments.

In some embodiments, selection of materials with predictable and favorable thermal expansion coefficients may minimize the potential under and over delivery of fluids as discussed above. In some embodiments, the syringe material, for example, may be selected to match the thermal expansion of the fluid. For example, the linear expansion coefficient for water at about 20 C is about:

$$68.9 \times 10^{-6} \frac{cm}{cm \cdot K} \quad [EQ\#4]$$

Thus, the syringe material may be selected to have an expansion coefficient close to this value. For example, a blend of polycarbonate and acrylonitrile butadiene styrene (also referred to as "ABS") could be used to match the thermal expansion coefficient of the fluid. In some embodiments, other plastics, for example, but not limited to, polycarbonate, may be close to the correct expansion coefficient such that the volume delivered by the syringe pump due to the expected temperature change is minimal and/or acceptable. In some embodiments, the plastic or material selected may be tailored to the slope of the thermal expansion of the fluid.

In some embodiments, the material of the plunger and/or the plunger rod may be selected to thermally differentially compensate for the change in temperature. In some embodiments, the materials for the syringe, plunger and plunger rod may be selected to thermally differentially compensate for the change in temperature. Also, or in addition to, in some embodiments, the material of one or more components of the drive train, or any other component of the infusion pump, may be selected to thermally differentially compensate for the change in temperature.

In some embodiments, the materials for any one or more infusion pump components may be selected to have an opposite thermal coefficient, or a thermally compensating material to minimize the thermal expansion effects of the temperature. For example, in higher temperatures, where the infusion pumps syringe expands, the flow of fluid may be negative. In some embodiments, at least one component of the drive train may have a negative thermal constant, thus, having the opposite thermal coefficient. Thus, upon a temperature increase, the syringe does not experience a change in volume.

In some embodiments, the use of a material which may undergo a phase change during a temperature change event may minimize the effect of the temperature differential/change on the infusion pump. For example, in some embodiments, the plunger may include a predetermined volume of wax, thus, as the temperature increases, the length or position may increase due to the phase change of the wax. Additional wax features may be added in some embodiments to prevent flow. In some embodiments, a wax feature may be added to move the plunger forward a (predetermined) distance such that the resulting change in the volume is equal to the square root of the diameter of the plunger. Thus, in some embodiments, the use of a material which undergoes a phase change in response to temperature/temperature change/differential may be used to compensate for the change of volume of the syringe due to a temperature change. In some embodiments, the material which undergoes a phase change in response to a temperature change may absorb the energy of the thermal differential, thus, for example, where the temperature is increasing, rather than rising the temperature of the infusion pump, the wax, or other phase change material, may melt the wax/phase change material, thus, acting as an energy sink and absorbing the heat.

In some embodiments, the syringe may be constrained in such a way that a change in temperature may cause the plunger to be advanced or withdrawn to compensate for the volume change of the syringe. For example, in some embodiments, the syringe may be held in a metal case, the metals that may be used include but are not limited to, steel, aluminum, and/or any metal with a low coefficient of thermal expansion, which may include, but is not limited to, FeNi36, also known as INVAR®. The plunger may be made from a material that has a high coefficient of thermal expansion. Thus, in this example, a decrease in temperature may cause the syringe plunger to be withdrawn as the diameter of the syringe barrel is decreasing. Thus, balancing these effects, the change in the total volume may be minimized.

Characterization and Controls Compensation

In some embodiments, characterizing the effect of a change in temperature on the volume of fluid pumped by the infusion device may be completed. In this embodiment, the pump may be subjected to temperature variation (i.e., both positive and negative) and the corresponding response by the infusion pump may be recorded. The characterization may include, but is not limited to, varying rates of change (i.e., 1 degree Celsius per minute, and whether positive and negative, etc), total temperature variation (e.g., 10 degrees Celsius, 5 degrees Celsius, etc), and/or position of syringe plunger.

The infusion pump may include one or more devices and/or components and/or systems to determine the temperature. In some embodiments, the infusion pump may include one or more thermistors or other temperature sensors to determine the temperature. However, in other embodiments, various methods and/or devices and/or systems to determine the temperature, either directly or indirectly, may be used, including, but not limited to, one or more of the following: at least one resistance temperature device (RTD) and/or at least one non-contact infrared device (non-contact IR). The location of the one or more thermistors and/or temperature determination devices may vary. The locations of one of more of the thermistors and/or temperature determination devices may include, but is not limited to, the drive screw, any location on the drive train, on the syringe barrel, including but not limited to, printed on the syringe barrel, the plunger and/or, the printed circuit board. In various embodiments, the one or more thermistor(s) and/or temperature determination devices location may be any where away from the heat sources that would render a potentially false reading. In some embodiments, the one or more thermistors may determine the temperature of one or more locations, including, but not limited to, inside of the syringe, the outside of the syringe, the inside of the pump, and/or the outside of the pump. Various controls may be determined based on a temperature model in any one or more of these locations. Thus, in some embodiments, the characterization may be made by taking temperature readings both within the syringe and outside of the syringe. In other embodiments, the characterization may be performed by taking temperature readings from outside the pump and inside the pump. In the various embodiments, the one or more thermistors and/or temperature determination devices are preferably placed in the same location on the pump for use by the user as they were during the characterization.

In some embodiments, the characterization may be completed by measuring the volume of fluid delivered as a function of temperature. In some embodiments, this may be accomplished by using a thermal chamber and an infusion set/cannula connected to the reservoir/syringe delivering fluid to a precision scale. However, in other embodiments, this may completed by using a thermal chamber and an infusion set/cannula connected to the reservoir/syringe delivering fluid, and following, determining the position of the plunger inside the reservoir to determine the total volume of fluid delivered.

In some embodiments, in practice, the temperature of the pump (in one or more locations and/or taken by one or more thermistors) may be measured and the target position of the plunger may vary as a function of temperature to compensate for the thermal expansion of the syringe and/or the plunger. The thermal expansion reading may be determined by referencing the characterization data, as discussed above. Thus, in some embodiments, the target position may be modified based on a look-up table or function approximation of the volume change of the syringe with temperature.

In some embodiments, the infusion pump delivers fluid either as a basal or a bolus delivery, and/or a variety thereof. The basal delivery is a programmed rate or volume per hour. The infusion pump delivers a volume of fluid at preset intervals for preset durations of time. The infusion pump may also deliver bolus volumes. A bolus is a requested volume of fluid delivered immediately, i.e., at the time the request is made. One embodiment of the bolus and basal delivery methods is described in PCT Application Serial No. PCT/US2009/060158, filed Oct. 9, 2009 and entitled Infusion Pump Assembly, now Publication No. WO 2010/042814, published Apr. 15, 2010 and entitled Infusion. Pump Assembly; and U.S. patent application Ser. No. 12/249,882, filed Oct. 10, 2008 and entitled Infusion Pump Assembly; now U.S. Publication No. US-2010-0094222, published Apr. 15, 2010 and entitled Infusion Pump Assembly, all of which are hereby incorporated herein by reference in their entireties. Further, in some embodiments, for example, in the embodiment described in U.S. Pat. No. 7,498,563, issued Mar. 3, 2009 and entitled Optical. Displacement Sensor for Infusion Devices, which is herein incorporated by reference in its entirety, the infusion pump may determine the distance the plunger must move to deliver a volume of fluid, e.g., a basal volume or a bolus volume. Thus, in some embodiments of the infusion pump system, the infusion pump may confirm the distance the plunger moved during a delivery using an optical displacement sensor. In some embodiments, the infusion pump determines the number of motor encoder counts per delivery and confirms movements of the plunger.

However, in various embodiments, the delivery method includes a determination of the distance the plunger should move (which may be referred to as the target plunger position) to deliver the desired/target volume. As discussed above, this may be done by determining the number of motor encoder steps, and in other embodiments, may be another method. Regardless, the infusion pump makes a determination of plunger distance movement.

One example of the characterization and controls compensation method is as follows. The first step may be to characterize the volume delivered as the temperature changes. This volume may be a function of the amount of fluid contained in the syringe, call this V, and, due to variations in the thermal expansion properties of plastics and liquids/fluids, also, a function of the temperature, call this T. A function, $\beta(T)$, may be found empirically that related the volume change to the temperature change.

$$\beta(T) = \frac{1}{V}\frac{\Delta V}{\Delta T} \quad [EQ\#5]$$

The coefficient β(T) may be approximated as a constant, found as a function of temperature (as shown above) or possible found as a function of both temperature and plunger position β(T, x).

Next, the target plunger position may be determined and adjusted. The target position, x, may be adjusted based on the following formula:

$$\Delta x = \frac{\beta(T)V}{\frac{\pi}{4}D^2}\Delta T \quad [EQ\#6]$$

Where D is the plunger diameter. If we substitute in $$V = \frac{\pi}{4}D^2 x$$

(assuming that x=0 where the plunger has reached the end of travel and displaced all of the fluid in the syringe) then the relationship may be simplified to:

$$\Delta x = \beta(T) x \Delta T \quad [EQ\#7]$$

In various embodiments, this correction may be performed in different ways, including, but not limited to, the following. In some embodiments, the correction may be done by delivering on an interval which may be more frequent than the basal delivery interval, which may be, but is not limited to, one delivery every e.g., 3 minutes, but in other embodiments, may be more frequent or less frequent. Further, the position of the syringe may be adjusted based on the temperature change, maintaining a zero net volume delivered between regular deliveries, e.g., basal and/or bolus deliveries. In some embodiments, this may be used for low basal rates, where the thermally driven volume may exceed the regularly scheduled basal delivery. This may, however, in some embodiments, require reversing the syringe direction to prevent delivery.

Another embodiment may include applying the correction when the fluid/insulin is scheduled for delivery. Thus, the target plunger position may be corrected based on the measured temperature change and estimated thermally-driven volume delivery. In some of these embodiments, the correction may be limited such that the plunger may only be driven in one direction.

In some embodiments, modeling may vary, and an assumption may be made with respect to both length and diameter of the syringe. In addition, assumption may be made regarding the effect of temperature on the thermal expansion coefficient of one or more components of the infusion pump, including, but not limited to, the drive train, plunger, plunger rod, infusion pump housing, and cannula.

In some embodiments, adjusting the plunger target may include adjusting the target so that it is closer to the exit of the syringe, or further away from the exit of the syringe. In some embodiments, the plunger advancement may be modified. In other embodiments, the plunger may be driven backwards to compensate for temperature. However, in some embodiments, depending on the infusion pump, it may be desired to limit adjustment to closer to the exit of the syringe. This may be due to the potential for backlash.

In some embodiments, a temperature dependant basal rate may be preprogrammed to the pump for temperature compensation. In these examples, the pump processor receives data from at least one temperature sensor. If the temperature data indicates that the temperature is such, or that the rate of change of temperature is such, that an adjustment should be made, the processor may signal to alter the preprogrammed basal rate. In some embodiments, this alteration may be either an additional or a decrease of the basal rate by a preset percentage, for example, an increase of 30% or a decrease of 15%. Of course, these are only examples, and in these embodiments, the preset alterations may be determined to be different from those stated.

In some embodiments, the infusion pump may include at least one temperature sensor and at least one optical sensor. In some embodiments, the optical sensor may be used to determine that the plunger advanced. In some embodiments, the distance of advancement may also be determined. In some embodiments, a small reflective optical sensor (hereinafter "optical sensor") that fits into the form factor of the infusion pump hardware is used. The optical sensor has a sensing range that overlaps with the plunger displacements. In the exemplary embodiment any optical sensor may be used, including, but not limited to a Sharp GP2S60, manufactured by Sharp Electronics Corporation which is a U.S. subsidiary of Sharp Corporation of Osaka, Japan. This optical sensor contains an infra red emitting diode and infra red sensing detector in a single package. Light from the emitter is unfocused and bounces off the sensing surface, some of which makes it back to the detector resulting in the sensed intensity of light that varies as a function of distance/angle to the reflector. In some embodiments, the sensor is placed such that the reflective surface is the plunger.

In some embodiments, an optical sensor may be used to determine the level of fluid in the syringe/reservoir. This information may be used to determine whether the plunger rod has advanced. Together with the temperature sensor information, this may provide added data/information to determine a temperature dependant change.

In some embodiments of the infusion pump system, including those embodiments disclosed and described in U.S. Pat. No. 7,498,563, issued Mar. 3, 2009 and entitled Optical Displacement Sensor for Infusion Devices, PCT Application Serial No. PCT/US2009/060158, filed Oct. 9, 2009 and entitled Infusion Pump Assembly, now Publication No. WO 2010/042814, published Apr. 15, 2010 and entitled Infusion Pump Assembly; and U.S. patent application Ser. No. 12/249,882, filed Oct. 10, 2008 and entitled Infusion Pump Assembly, now U.S. Publication No. US-2010-0094222, published Apr. 15, 2010 and entitled Infusion Pump Assembly, all of which are hereby incorporated herein by reference in their entireties, the infusion pump may include an optical displacement sensor. This sensor may be used to determine whether the plunger rod has advanced, either forward or backwards, and the distance of the advancement. Using this displacement information, together with the information from the one or more temperature sensors, the effect of the temperature change on the plunger may be determined. In turn, this determination may increase the accuracy of controls used to compensate for a temperature change. This may include, but is not limited to, decreasing the amount of fluid delivered due to a sensed forward movement and/or increasing the amount of fluid delivered due to a sensed backwards movement. In either case, the increase and/or decease of the basal rate and/or amount and/or the amount of bolus (for example, by a percentage of the amount intended) is by a predetermined amount and for a predetermined time.

In some embodiments, the infusion pump system may include a system and/or method for adjusting the basal rate and/or bolus amount based on a temperature change. Thus, in various embodiments, where the system determines that a threshold temperature change, either up or down, has occurred, the system may automatically, and/or by request and/or confirmation by the user, enter a mode having a limited period, e.g., a flat pre-set limited time period, e.g., 20 minutes, and/or in some embodiments, the mode may continue until the temperature change threshold is not longer applicable. In some embodiments, where, for example, a decreasing temperature gradient is a primary concern, the infusion pump processor may be pre-programmed with a "decreasing gradient" mode, and the infusion pump may purposefully under deliver in this mode, i.e., an automatic percentage decrease in the basal rate, and, in some embodiments, also, the bolus, may be instituted to compensate for a predicated additional delivery of fluid. As discussed above, determining the percentage change of insulin delivery may depend on the characterization of the infusion pump.

Following, in some embodiments, where, for example, increasing temperature gradient is the primary concern, the infusion pump processor may be pre-programmed with a "increasing temperature gradient" mode, and the infusion pump may purposefully over deliver, i.e., an automatic percentage increase in the basal rate, and, in some embodiments, also the bolus, may be instituted to compensate for the predicated decrease in delivery of fluid. As discussed above, determining the percentage change may depend on the characterization of the infusion pump.

Closed loop Temperature Compensation

For the purposes of this description, the term "advanced" refers to the movement of a plunger within a syringe or reservoir body. Advancement is not limited to movement in a particular direction. The syringe has an exit end, which is the end of the syringe in which fluid moves outward from the syringe.

In some embodiments, and referring again also to FIG. 4, the system may include one or more devices and/or sensors to determine the effect of the temperature on the syringe/plunger and/or the pumping of fluid, either towards the user/cannula or away from the user/cannula. These devices and/or sensors may include, but are not limited to, one or more flow sensors 451, one more occlusion devices and/or one or more binary valves 451, and/or one or more strain beams 412 or sensors and/or one or more optical sensors and/or one or more temperature sensors 453 and/or one or more ultrasonic range sensors and/or one or more potentiometers 455 and/or one or more rotor encoders and/or one or more linear encoders.

With respect to optical sensors, in some embodiments, the infusion pump may include at least one temperature sensor and at least one optical sensor. In some embodiments, the optical sensor may be used to determine that the plunger advanced. In some embodiments, the distance of advancement may also be determined. In some embodiments, a small reflective optical sensor (hereinafter "optical sensor") that fits into the form factor of the infusion pump hardware is used. In various embodiments, the optical sensor has a sensing range that overlaps with the plunger displacements. In various embodiments any optical sensor may be used, including, but not limited to one or more of the following: Sharp GP2S60, Sharp GP2S700 and Sharp GP2A240LC, all of which are manufactured by Sharp Electronics Corporation which is a U.S. subsidiary of Sharp Corporation of Osaka, Japan. This optical sensor contains an infra red emitting diode and infra red sensing detector in a single package. Light from the emitter is unfocused and bounces off the sensing surface, some of which makes it back to the detector resulting in the sensed intensity of light that varies as a function of distance/angle to the reflector. In some embodiments, the sensor is placed such that the reflective surface is the plunger.

In some embodiments, an optical sensor may be used to determine the level of fluid in the syringe/reservoir. This information may be used to determine whether the plunger rod has advanced. Together with the temperature sensor information, this may provide added data/information to determine a temperature dependant change.

In some embodiments of the infusion pump system, the infusion pump may include an optical displacement sensor. This sensor may be used to determine whether the plunger rod has advanced, either forward (towards the syringe exit) or backwards (away from the syringe exit), and the distance of the advancement. Using this displacement information, together with the information from the one or more temperature sensors, the effect of the temperature change on the plunger may be determined. In turn, this determination may increase the accuracy of controls used to compensate for a temperature change. This may include, but is not limited to, decreasing the amount of fluid delivered (i.e., decreasing the volume of fluid that was scheduled to be delivered, i.e., basal rate, or requested to be delivered, i.e., bolus amount) to a sensed forward movement and/or increasing the amount of fluid delivered due to a sensed backwards movement.

In some embodiments, the infusion pump may include an exit valve and/or an occluder. Thus, in these embodiments, the infusion pump includes at least one device to prevent the delivery of fluid either from the syringe to the cannula and/or from the cannula to the user. In some embodiments, the device is activated when the at least one temperature sensor sends a signal to the processor and the processor determines that the temperature change meets a threshold, i.e., that the temperature change is large enough to effect a change in delivery due to temperature. In some embodiments, this may activate the occluder and/or exit valve, preventing fluid from flowing into or out of the syringe and/or the cannula. In some embodiments, the occluder and/or exit valve device is deactivated when the at least one temperature sensor sends a signal to the processor and the processor determines that the temperature change no longer meets a threshold, i.e., that the temperature change is no longer large enough to effect a change in delivery due to temperature. In some embodiments, this may deactivate the occluder and/or exit valve, allowing fluid to flow out of the syringe and/or to the cannula and/or to the user. Again, as discussed above, in some embodiments, the plunger target may be adjusted in response to the information from one or more temperature sensors.

In some embodiments, the occluder/exit valve may be closed during the interval when the infusion pump is not actively delivering fluid so as to prevent inadvertent fluid flow in or out of the syringe/reservoir due to a change in temperature. During the time when the infusion pump is not actively delivering fluid, the at least one temperature sensor may continue to send signals to the processor indicating temperature. This information may be used by the control system to determine whether and how to modify the "next delivery" of fluid, i.e., the next plunger target. Thus, when the "next delivery" is made, the occluder/exit valve may open and the fluid is delivered.

Thus, in these embodiments, the occluder/exit valve may act primarily to prevent spontaneous unintended fluid flow that may be caused by temperature change. The control system may adjust the volume delivery, i.e., plunger target, based on the temperature change such that the volume of delivered fluid compensates for the temperature change.

In some embodiments, the infusion pump may include a compliant component. In some embodiments, the compliant component may allow the difference in volume change in the syringe/reservoir while maintaining a pressure constant. Thus, in these embodiments, controller compensation may not be necessary to compensate for temperature change when the occluder/exit valve is open as there would not be a pressure build up from a change in temperature.

In some embodiments, once a threshold temperature change has been determined, the occluder/exit valve may be closed and the plunger rod may be allowed to float, i.e., the plunger rod may become disengaged with the drive train. A change in pressure would thus allow the plunger to float and find equilibrium, thus adjusting without the need for controller compensation in response to a temperature change.

In some embodiments, the infusion pump may include at least one flow sensor, including, but not limited to, a flow sensor positioned in the exit fluid path. The flow sensor may detect the flow of fluid. This information may be correlated with delivery instructions and a determination may be made whether the fluid delivered was requested and/or a proper delivery. In some embodiments, where flow is detected and it is determined that the fluid delivered was not requested and/or not a proper delivery, the occluder and/or exit valve may be closed. Thus, in some embodiments, a flow sensor may determine fluid flow, either inward or outward, and where this is not an expect event, the infusion pump may activate at least one mechanism, including, but not limited to, an occluder and/or a valve to prevent the continued flow of fluid. Additionally, the flow information may be used to determine the amount or volume of fluid that has been delivered or has flowed inward and this information may be used to alter the plunger target during the next scheduled or requested delivery (e.g., basal or bolus), or, in some embodiments, may be used to alter the delivery schedule. In some embodiments, this may be completed without user interaction. In some embodiments, an alert may be sent to the user and the user must accept the proposed course or action to alleviate the under or over delivery of fluid.

In some embodiments, the infusion pump may include one or more optical sensors. These sensors may be placed in the infusion pump to determine the level of fluid in the syringe/reservoir. The one or more optical sensors may determine the level of fluid before the processor signals the drive train to advance the plunger and after. Thus, the volume difference may be determined before and after the plunger is advanced. However, the at least one optical sensor may, in some embodiments, collect data a preset intervals, regardless or whether the drive train has been activated. Thus, the at least one optical sensor may collect information to determine when and whether the plunger has advances and/or when and whether fluid has been delivered or pulled in. Thus, the at least one optical sensor may collect data for the processor to determine when a non-requested delivery event may have occurred. The processor may correlate this information with the at least one temperature sensor and thereby determine whether the infusion pump is experiencing a temperature related effect. In some embodiments, the processor may alert the user. In some embodiments, the information may be used to instigate a control algorithm to compensate for the temperature change effect using, for example, but not limited to, the various embodiments discussed herein.

In some embodiments, a strain beam may be used to identify a plunger moving away from the exit of the syringe. In these embodiments, the strain beam may be positioned relative to the plunger rod such that where the plunger rod begins to move away from the syringe exit, the strain beam will sense the strain. In some embodiments of the infusion pump system, the infusion pump includes a strain beam that may be used to detect and/or identify occlusions. The strain beam and methods may be, in some embodiments, similar to those described in U.S. patent application Ser. No. 12/249,882, filed Oct. 10, 2008 and entitled Infusion Pump Assembly, now U.S. Publication No. US-2010-0094222, published Apr. 15, 2010 and entitled Infusion Pump Assembly; and PCT Application Serial No. PCT/US2009/060158, filed Oct. 9, 2009 and entitled Infusion Pump Assembly, now Publication No. WO 2010/042814, published. Apr. 15, 2010 and entitled Infusion Pump Assembly, all of which are hereby incorporated herein by reference in their entireties, which are hereby incorporated herein by reference in their entireties. However, together with the at least one temperature sensor, a strain beam may determine whether a particular temperature change has resulted in plunger movement. Where plunger movement is detected due to a temperature change, the infusion pump may alert the user. In some embodiments, the system may correlate a change in strain with a change in temperature.

Temperature Maintenance

As discussed above, there may be a desire to maintain the temperature of an infusion pump to avoid any consequences from a temperature change. In some embodiments, to minimize or prevent the above-described effects of temperature changes on the infusion pump and delivery of fluid, one or more various apparatus and/or systems may be employed to maintain the temperature of the infusion pump.

In some embodiments, the infusion pump includes a heater device. The heater device may receive instructions from the processor. The heater device may be located anywhere in or on the infusion pump, however, in some embodiments, the heater device is located within the infusion pump housing. In some embodiments, the heater device is powered by a power source or battery inside the infusion pump. However, in some embodiments, the power source may be outside the infusion pump.

The heater source may be any heating source desired, however, in the exemplary embodiment, the heating source may be a KAPTON® (Polyimide Film) Heater kit, part number KH-KIT-EFH-15001 and available from Omega.com®. In some embodiments, at least one temperature sensor is located in or on the infusion pump. The at least one temperature sensor communicates information to the processor. Based on the temperature sensor data, the processor may act as a thermostat and power the heater source to maintain the temperature in the infusion pump at a desired temperature. In some embodiments, the desired temperature may be between 15 and 30 degrees Celsius, but in other embodiments, the maintenance temperature may be different. In some embodiments, it may be desirable to maintain the temperature at the higher end.

In some embodiments the syringe/reservoir may be contained in a metal case in the infusion pump. The metal case may increase the conduction of heat between the heater element and the syringe reservoir.

In some embodiments, the at least one heater element may be located in one or more locations inside the infusion pump and one or more of these locations may be selected to maintain the temperature of one or more components of the infusion pump, including, but not limited to, the syringe, fluid, plunger, housing, plunger rod and/or the drive train.

In some embodiments, the at least one heater elements may additionally increase the power source and/or battery life in the infusion pump. Maintaining the temperature at or about 35 degrees Celsius may be beneficial to battery life and/or performance.

In some embodiments, it may be desirable to utilize the user's body as a heat sink, wearing the infusion pump close to the user's skin. This may be accomplished using various devices and apparatus, including but not limited to one or more of the following.

A hook and loop system fastener system, for example, but not limited to one offered by VELCRO® USA Inc. of Manchester, N.H., may be utilized to allow for easy attachment/removal of an infusion pump from the user. Accordingly, an adhesive patch may be attached to the skin of the user and may include an outward facing hook or loop surface. Additionally, a surface of infusion pump 114 may include a complementary hook or loop surface. Depending upon the separation resistance of the particular type of hook and loop fastener system employed, it may be possible for the strength of the hook and loop connection to be stronger than the strength of the adhesive to skin connection. Accordingly, various hook and loop surface patterns may be utilized to regulate the strength of the hook and loop connection.

Figure 4A:
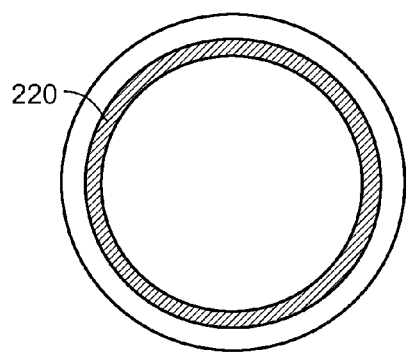
FIGS. 4A-4E depict a plurality of hook-and-loop fastener configurations according to some embodiments.
Figure 4B:
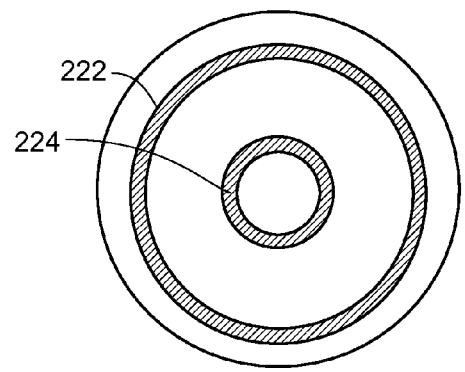
Figure 4C:
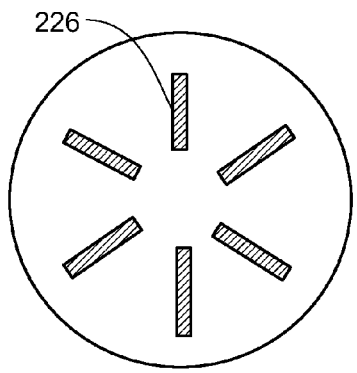
Figure 4D:
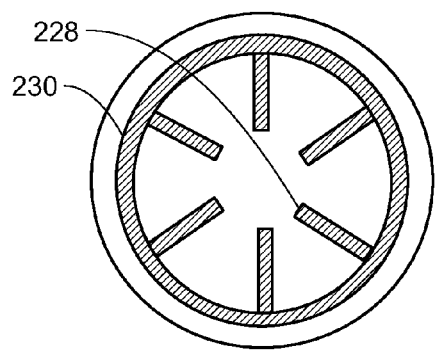
Figure 4E:
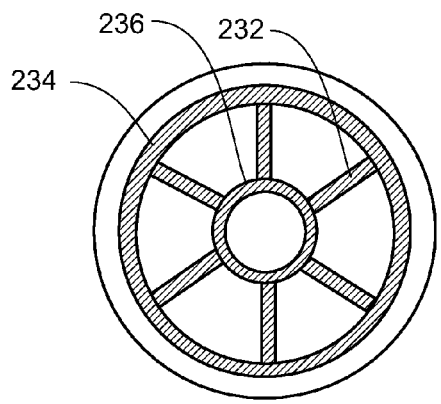

Referring also to FIGS. 4A-4E, five examples of such hook and loop surface patterns are shown. Assume for illustrative purposes that one surface of infusion pump housing is covered in a "loop" material. Accordingly, the strength of the hook and loop connection may be regulated by varying the pattern (i.e., amount) of the "hook" material present on the surface of adhesive patch. Examples of such patterns may include but are not limited to: a singular outer circle 220 of "hook" material (as shown in FIG. 4A); a plurality of concentric circles 222, 224 of "hook" material (as shown in FIG. 4B); a plurality of radial spokes 226 of "hook" material (as shown in FIG. 4C); a plurality of radial spokes 228 of "hook" material in combination with a single outer circle 230 of "hook" material (as shown in FIG. 4D); and a plurality of radial spokes 232 of "hook" material in combination with a plurality of concentric circles 234, 236 of "hook" material (as shown in FIG. 4E).

In another embodiment, a holder, pouch, sack, container or other type of housing (generally referred to as a "holder") may be sized to accommodate an infusion pump. In some embodiments, the holder may be constructed to include multiple layers including but not limited to, one or more insulating layers. In some embodiments, one or more of the layers may include a fabric that when wetted and refrigerated or frozen, the layer provides a cooling effect. This layer may be desired in warmer climates or in situations where the user's infusion pump may be exposed to the sun or a warm environment. In some embodiments, the one or more layers of material may be highly absorbent material. In some embodiments, the holder may include one or more canisters of isopropyl alcohol which may, when deployed, be absorbed into the highly absorbent material of the holder and provide evaporative cooling to the infusion pump. In various embodiments, the holder may include alternative and/or additional methods, systems and/or devices for cooling the infusion pump.

In some embodiments, the holder may include one or more temperature measurement devices and/or temperature sensors that may transmit information to the infusion pump and/or a controller. The one or more temperature sensors may communicate the temperature of the holder and either deploy the one or more canisters of alcohol and or alert the infusion pump/user/controller and/or turn o the heating source, based on the temperature sensor. In some embodiments, the heating and/or cooling may be triggered by reaching a threshold change in temperature. Thus, in some embodiments, the holder may provide for a closed-loop system for maintaining the temperature for the infusion pump.

Figure 5:
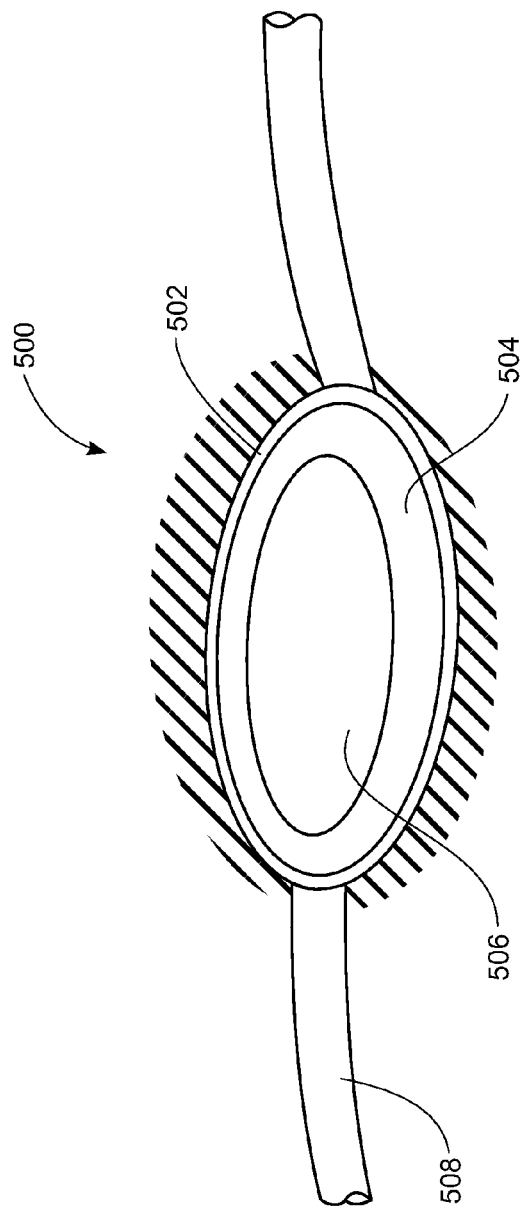
FIG. 5 is an illustration of one embodiment of a holder.

Referring now to FIG. 5, some embodiments of the holder 500 include an outside layer 502, an inside layer 504 and an inner pocket 506. The pocket 506 may include additional cushion or insulation to both protect the infusion pump from outside forces and/or temperature change. The holder 500 may include a fastener along the front, top or the side. In some embodiments, the holder 500 may include the holder may include a pull down flap (not shown) on the front to expose the screen and/or input assemblies (e.g., including but not limited to buttons, sliders, and/or jog wheels). In some embodiments, the flap may be secured closed using a hook-and-loop system. In other embodiments, the flap may be secured using any other fastener system including, but not limited to, snaps, buttons, magnetic closures and zippers.

In some embodiments, the holder 500 may be attached to a strap 508 designed to be attached to the user (see FIG. 6 for example). However, in various embodiments, the strap 508 may be elastic and/or adjustable and may include at least one closure device. Although shown in FIG. 6 as being worn about the mid section of a user 510, the holder 500 may be worn anywhere the user desires.

Figure 7:
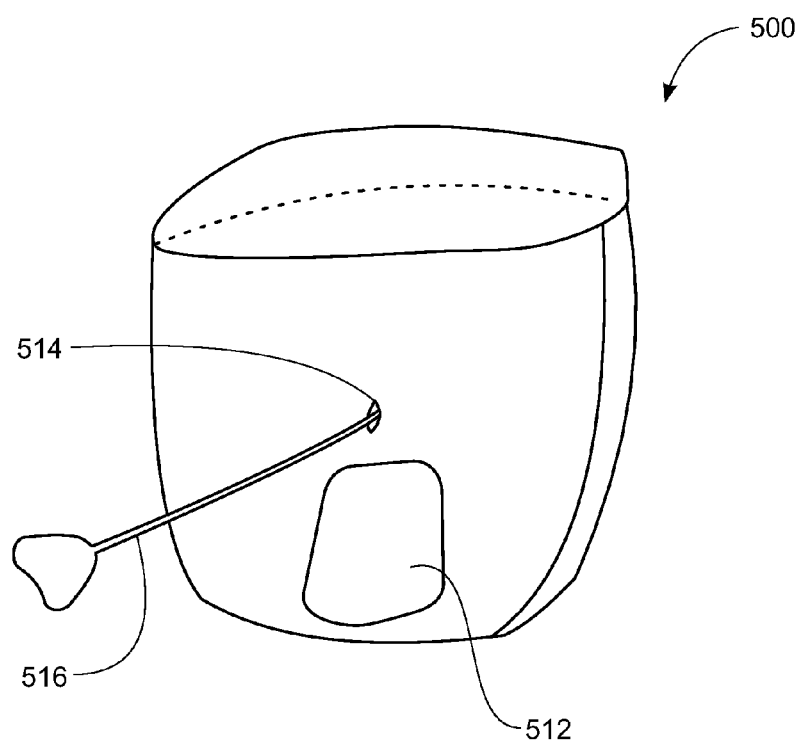
FIG. 7 is an illustration of one embodiment of the back of a holder.

Referring now to FIG. 7, an embodiment of the back of the holder 500 is shown. In some embodiments, the holder may include a clip 512 which may be referred to as a "belt-clip" or another type of clip configured such that it securely and removably fits over a belt, handle, piece of clothing or other. In some embodiments, the holder 500 may additionally include an opening 514 for tubing 516 to fit through. In some embodiments, the infusion pump (not shown) may be contained inside the holder 500 and the holder worn close to the insertion site (not shown) on the user such that minimal tubing 516 is exposed to the outside temperature. Thus, embodiments of the holder 500 including an opening 514 for tubing may be beneficial for maintaining the temperature of the tubing 516 and/or the fluid in the tubing.

In some embodiments, a plastic material for example, a Press n' Seal, or another material of similar behavior, may be used to attach and maintain the infusion pump against the user's body. In other embodiments, a cuff or band fitted against the leg, midsection or arm, for example, of a user may include a pouch for the infusion pump. In other embodiments, the infusion pump may be maintained in position against the skin through inner pockets, bra pockets, etc.

Various embodiments are described herein for both utilizing the user's body heat and/or a heating element to maintain the temperature of the infusion pump. However, additional devices and apparatus are within the scope of the invention. Further, various methods, systems and apparatus for maintaining the temperature of an infusion pump may include at least one temperature sensor.

Insulin Temperature

Described herein are various methods, systems, devices and/or apparatus for maintaining the temperature of an infusion pump. Inherent in at least some of these embodiments is the maintenance of the infusible fluid/insulin temperature. It is well know that manufacturers of insulin recommend that the temperature of insulin not exceed a high and a low temperature. Additionally, it may be beneficial to maintain fast-acting (e.g., HUMALOG®, NOVOLOG®) at room/ambient temperature (e.g., between 59 and 86 degrees Fahrenheit) once the vial has been used, i.e., the manufacturer recommends storing insulin in a refrigerated area, e.g., between 36 and 46 degrees Fahrenheit, until the vial is used. From that point on, it is recommended that the vial be stored at room temperature.

As insulin may be less effective or not effective once it has reached a non-recommended temperature, it may be beneficial for a user to know whether the insulin has been properly stored, whether while in transit, in the refrigerator or while in use.

Figure 8:
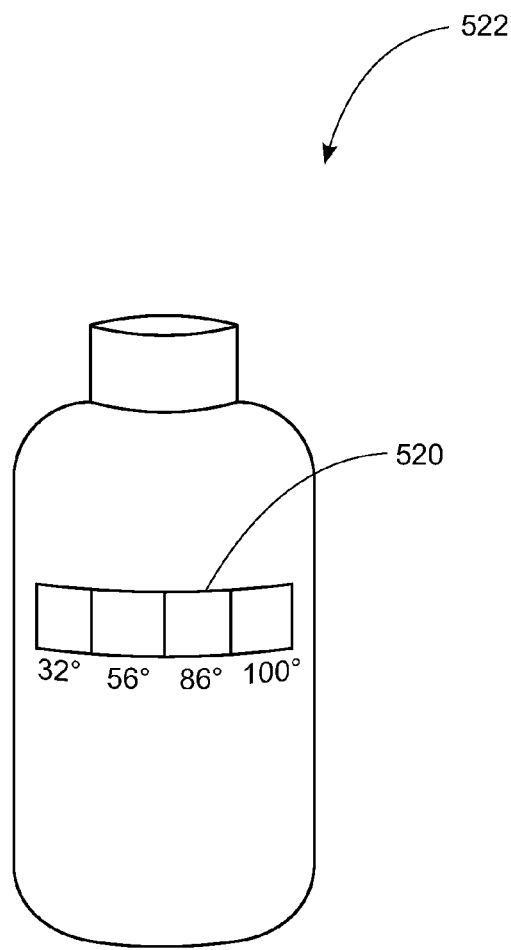
FIG. 8 is an illustration of one embodiment of a vial with a temperature gauge/label.

Referring to FIG. 8, in one embodiment, a stick-on temperature gauge 520 may be placed on a vial 522 of fluid, and in some embodiments, on a vial of insulin. The gauge may tell the user the current temperature of the vial. In some embodiments, the temperature may be indicated as various shades of red and blue, indicating various temperatures towards the high and low range. In some embodiments, once the temperature has reached either the maximum or minimum temperature (which is predetermined and may, in some embodiments, be 35 and 87 Fahrenheit respectively), the gauge becomes non-reversible, thus indicating instantly to the user that the insulin has reached either a maximum or minimum temperature.

Any stick-on temperature gauge may be used including a non-reversible temperature label such as a Non-Reversible Temperature Labels, 3 Temperature Ranges, part number TL-3 available from Omega.com®, or another similar temperature label. As discussed above, in some embodiments, a Reversible Temperature Label may be used or a label with both reversible and non-reversible components.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. An infusion pump system comprising:
a syringe having a plunger movable within a syringe barrel, the syringe having an exit end;
at least one temperature determination device adjacent to the syringe;
at least one device to determine the distance the plunger has moved with respect to the syringe barrel; and
a pump processor in communication with the at least one temperature determination device and the at least one optical sensor,
wherein when the pump processor determines a change in temperature and a corresponding plunger movement, the pump processor increases or decreases a preprogrammed basal rate of the infusion pump by a predetermined amount for a predetermined time.

2. The system of claim 1 further comprising wherein when the pump processor determines an upward change in temperature and a corresponding plunger movement away from the syringe exit, the pump processor increases the preprogrammed basal rate of the infusion pump by a predetermined amount for a predetermined time.

3. The system of claim 1 further comprising wherein when the pump processor determines an downward change in temperature and a corresponding plunger movement towards the syringe exit, the pump processor decreases the preprogrammed basal rate of the infusion pump by a predetermined amount for a predetermined time.

4. The system of claim 1 further comprising wherein the at least one temperature determination device is a thermistor.

5. The system of claim 1 further comprising wherein the at least one device to determine the distance the plunger has moved with respect to the syringe barrel is an optical sensor.

6. An infusion pump system comprising:
a syringe having an exit end and a plunger movable within the syringe;
at least one temperature determination device;
at least one device to determine the effect of a temperature change on the movement of the plunger; and
a pump processor to compensate for the movement of the plunger based on a temperature change.

7. The system of claim 6 wherein the pump processor commands the plunger to move away from the syringe exit by a predetermined distance to compensate for the movement of the plunger based on a temperature change.

8. The system of clam 6 wherein the pump processor decreases a preprogrammed basal rate for a predetermined amount of time by a predetermined amount based on the movement of the plunger based on a temperature change.

9. The system of claim 6 wherein the at least one temperature determination device is located adjacent to the syringe.

10. The system of claim 6 wherein the at least one temperature determination device is a thermistor.

11. The system of claim 6 wherein the at least one device to determine the effect of the temperature change on the movement of the plunger is an optical sensor.

12. An infusion pump system comprising:
a syringe having an exit end and a plunger movable within the syringe;
at least one temperature determination device;
at least one device to detect the effect of a temperature change on the movement of the plunger; and
a pump processor in communication with the at least one temperature determination device and the at least one device to detect the effect of a temperature change on the movement of the plunger.

13. The system of claim 12 wherein the at least one device to detect the effect of a temperature change on the movement of the plunger is a flow sensor located downstream from the syringe exit.

14. The system of claim 12 wherein the at least one device to detect the effect of a temperature change on the movement of the plunger is an occlusion device located downstream from the syringe exit wherein the occlusion device occludes a flow path, the occlusion device controlled by the pump processor.

15. The system of claim 12 wherein the at least one device to detect the effect of a temperature change on the movement of the plunger is at least one binary valve located downstream from the syringe exit wherein the at least one binary valve occludes a flow path, the at least one binary valve controlled by the pump processor.

16. The system of claim 12 wherein the at least one device to detect the effect of a temperature change on the movement of the plunger is a strain beam located in force relationship with the plunger.

17. The system of claim 12 wherein the at least one device to detect the effect of a temperature change on the movement of the plunger is at least one potentiometer.

18. The system of claim 12 wherein the plunger further comprising a predetermined volume of a material which undergoes a phase change during a temperature change event.

19. The system of claim 18 wherein the material is wax and the wax and wherein the wax undergoes a phase change, moves the plunger forward a predetermined distance whereby the resulting change compensates for the change in volume of the syringe due to a temperature change.

20. An infusion pump system comprising:
a syringe having an exit end and a plunger movable within the syringe;
an occluder located downstream from the syringe exit;
at least one temperature determination device; and
a pump processor in communication with the occluder and the at least one temperature determination device, wherein the pump processor activates the occluder based on the temperature signals from the at least one temperature determination device.

21. The system of claim 20 wherein when the at least one temperature determination device signal indicates a temperature change that exceeds a predetermined threshold, the pump processor activates the occluder.

22. The system of claim 20 wherein the pump controller activates the occluder between pump deliveries.

* * * * *